United States Patent [19]

Szalay et al.

[11] Patent Number: 4,960,913
[45] Date of Patent: Oct. 2, 1990

[54] PROCESS FOR THE PREPARATION OF PHARMACEUTICAL COMPOSITIONS

[75] Inventors: Erzsébet Szalay, Budapest; György Lugosi, Göd-felso; Tamás U. Kállay, Budapest; Zsuzsanna Nád, Budapest; István Jelinek, Budapest; Vilmos Simonidesz, Budapest; Péter Gyory, Budapest; Lajos Nagy, Szentendre; Márta Lugosi, Göd-felso; Ilona Sánta née Singola, Budapest; Gábor Besenyei, Budapest; László Simándi, Budapest, all of Hungary

[73] Assignee: Chinoin Gyogyszer- es Vegyeszeti Termekek Gyara Rt., Budapest, Hungary

[21] Appl. No.: 353,657

[22] PCT Filed: Sep. 16, 1988

[86] PCT No.: PCT/HU88/00063
§ 371 Date: May 5, 1989
§ 102(e) Date: May 5, 1989

[87] PCT Pub. No.: WO89/02429
PCT Pub. Date: Mar. 23, 1989

[30] Foreign Application Priority Data

Sep. 18, 1987 [HU] Hungary ............... 4164/87

[51] Int. Cl.⁵ .................................. C07C 237/26
[52] U.S. Cl. .................................. 552/206; 502/215
[58] Field of Search .............. 552/206; 502/215

[56] References Cited

U.S. PATENT DOCUMENTS

| | | | |
|---|---|---|---|
| 3,962,139 | 6/1976 | Moesdijk et al. | 502/215 |
| 4,061,676 | 12/1977 | Villax | 552/206 |
| 4,066,694 | 1/1978 | Blackwood et al. | 552/202 |
| 4,597,904 | 7/1986 | Page | 552/207 |
| 4,743,699 | 5/1988 | Page et al. | 552/203 |
| 4,902,447 | 2/1990 | Khanna et al. | 552/207 |
| 4,911,865 | 3/1990 | Heggie et al. | 552/207 |

FOREIGN PATENT DOCUMENTS 67210 10/1984 Finland .

Primary Examiner—Richard L. Raymond
Assistant Examiner—Raymond Covington
Attorney, Agent, or Firm—Herbert Dubno; Jonathan Myers

[57] ABSTRACT

The invention relates to a process for the preparation of tetracycline derivatives of the formula

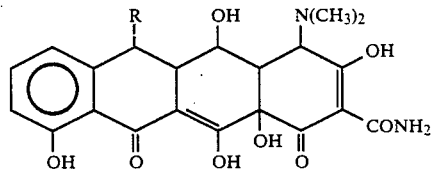

and acid addition salts thereof —wherein R stands for —CH₃ or =CH₂—by dehalogenating and hydrogenating chloromethacycline or acid addition salt thereof of the formula

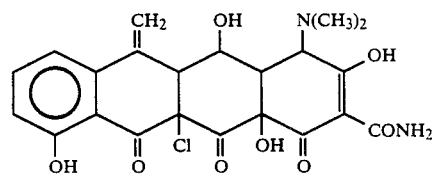

or by hydrating methacycline or acid addition salts thereof of the formula

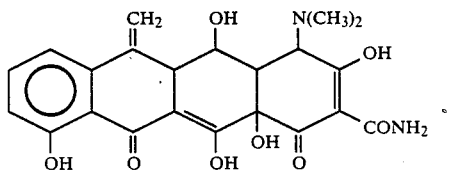

by treatment with hydrogen gas in the presence of a noble metal alloy catalyst on carrier and organic solvent which comprises performing, hydrogenating under pressure of 0.1–1.0 MPa with an alloy catalyst consisting of the alloy palladium or platinum and selenium and/or tellurium used at a ratio of 1:0.01–0.5 related to the amount of the starting tetracycline and carrying out, if desired dehalogenation and hydrogenation in one step.

6 Claims, No Drawings

PROCESS FOR THE PREPARATION OF PHARMACEUTICAL COMPOSITIONS

SPECIFICATION INVENTION

The present invention relates to an improved process for the preparation of doxycycline and methacycline and acid addition salts thereof by catalytic dehalogenation and hydrogenation by using a tellurium and/or selenium containing alloy catalyst, the latter being prepared according to this invention as well.

The following abbreviations are used throughout the specification:

"methacycline": 4-dimethylamino-1,4,4a,5,5a,6,11,12a-octahydro-3,5,10,12,12a-pentahydroxy-6-methylene-1,11-dioxo-2-naphthacene-carboxamide of the formula

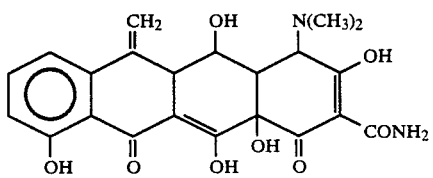

III.

"chloro-methacycline": 4-dimethylamino-1,4,4a,5-,5a,6,11,12-12a-nonahydro-3,5,10,12a-tetrahydroxy-11a-chloro-6-methylene-1,11,12-trioxo-2-naphthacene-carboxamide of the formula

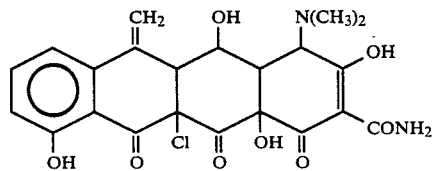

II.

"doxycycline": α-6-desoxy-5-hydroxy-tetracycline, i.e. 4-dimethylamino-1,4,4a,5,5a,6,11,12a-octahydro-3,5,10,12-12a-pentahydroxy-6α-methyl-1,11-dioxo-2-naphthacene-carboxamide of the formula

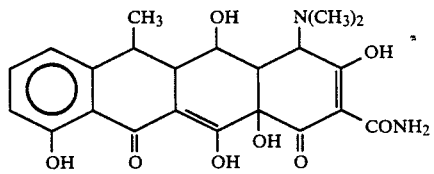

IV.

"β-doxycycline" is the β-isomer of doxycycline R stands for —CH₃ or =CH₂

BACKGROUND OF THE INVENTION

It is known that methacycline and doxycycline are very effective representatives of tetracycline type antibiotics.

Several processes are known for the preparation thereof using oxytetracycline as starting material and preparing chloromethacycline followed by dehalogenation and if desired by hydrogenation the obtained methacycline to doxycycline.

Dehalogenation was accomplished—among other methods—by introducing hydrogen gas in the presence of a catalyst, see e.g. Example 9 of Hungarian Patent No. 150909, wherein rhodium precipitated on active carbon was used.

This process, however, was not satisfactory as reaction products were produced which were difficult to separate from by-products and the conversion was not complete either. Therefore the use of secondary or tertiary phosphines has been recommended in Hungarian Patent No. 169 605. This process was accompanied with the disadvantage that an equimolar amount of tertiary or secondary phosphines was needed, resulting in a great amount of poisonous waste, and the formed phosphine oxide could be converted again to phosphine only by a multi-step reaction.

The introduction of hydrogen gas in the presence of a catalyst was also used for the saturation of the double bond of the methylene group at the 6-position on methacycline in order to produce doxycycline.

In the course of hydrogenation 6-desoxy-5-hydroxy-tetracycline of the formula (IV) can occur in the form of α- and β-isomers. Only the α-isomer is valuable as medicine, i.e. doxycycline. The amount of the α-isomers during hydrogenation determines if the hydrogenation process is successful, i.e. if hydrogenation can be carried out selectively, to produce mainly α-isomer with a good yield and pure quality.

It is also known that 6-desoxy-5-hydroxy-tetracycline can be prepared with a yield of 60% by using a 5% palladium or rhodium catalyst on a carrier, but the product was a 1:1 mixture of α- and β-isomers, which was followed by the separation of the α-isomer accompanied by further losses (U.S. Pat. No. 3,200,149). The ratio of the formation of the α-isomer can considerably be improved, if the noble metal catalyst on a carrier is poisoned by carbon monoxide, quinoline sulphur or other sulphur compounds. Thus the yield of the α-isomer could be increased to 40–50%, but even so the product had to be further purified due to the remaining 10% β-isomer impurities (Hungarian Patent No. 156 925). In order to improve the stereoselectivity of hydrogenation an alloy catalyst consisting of the metals of platinum group, copper, silver or gold has been used and a doxycycline yield of about 70% has been disclosed with 1 to 10% β-isomer impurities (Hungarian Patent No. 167 250).

A 92% α-isomer content has been achieved by using a catalyst containing palladium atoms located on ultramicroporous active carbon, without poisoning, with a yield of 76% (Hungarian Patent No. 169 667).

Hydrogenation could be performed by using Raney nickel and Raney cobalt as a catalyst according to GB-PS No. 1 296 340, but the formation of α-isomer in the reaction mixtures amounted only to about 40%. According to Finnish Patent No. 67210 to palladium/-charcoal catalyst a complex of bis(diphenylselenide) palladium(II)chloride was added resulting thus in a yield of 75%, wherein the ratio of the α-isomer was about 95%. According to the disclosure this effect could not be achieved if diphenylselenide was not used in a complex form.

In order to give a complete review of the known processes, we mention those hydrogenation processes, which are not close to our process, but wherein hydrogenation was performed by using triphenyl phosphine rhodium complexes, being catalysts which are soluble in the reaction mixture (DE-OS No. 2 403 714) or by using further additives next to the complexes (Hungarian Patent Nos. 169 753, 169 508, 173 508 and 187 465).

Doxycycline could thus be prepared with a good yield and selectivity.

Inspite of the significant development the known processes show many drawbacks. As already mentioned the use of the known heterogeneous catalysts only partially solves the problem of stereoselectivity. A considerable amount of these catalysts had to be used, and so the ratio substrate-catalyst was not favorable. The relative great amount of the used solvent was also unfavorable. Although the catalysts can be removed from the reaction mixture by filtration, the solvent has to be recovered before use by a costly and inefficient procedure.

In the case of homogenous catalysis the catalyst is in solution and its isolation is not easy. Rhodium is very expensive, it is difficult to obtain, its recovery is complicated, expensive and it can contaminate the product.

According to the present invention methacycline and doxycycline are prepared in a heterogeneous layer, wherein dehalogenation can be performed with good yield and reduction takes place stereoselectivetly and the side reactions can be eliminated to such extent that no extra purification of the product is needed and the used catalyst can be prepared simply and the specific costs of the catalyst are low. Dehalogenation and hydrogenation can be effected without any extra equipment by using the same type of catalyst. Thus the needed medicine can be prepared.

SUMMARY OF THE INVENTION

The present invention is directed to a process for the preparation of tetracycline derivatives and acid addition salts thereof of the formula (I)

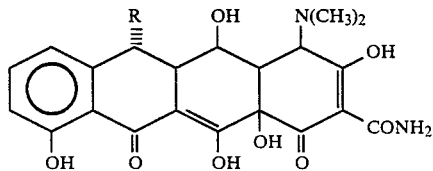

by dehalogenating and hydrogenation chloromethacycline or acid addition salt thereof of the formula II or by hydrogenation methacycline or acid addition salt thereof of the formula III by a treatment of thereof with hydrogen gas in the presence of a noble metal alloy catalyst on a carrier in the presence of an organic solvent comprising carrying out the hydrogenation at a pressure of 0.1–1.0 MPa with an alloy catalyst used at a ratio of 1:0.01–0.5 related to the starting tetracycline derivative consisting of an alloy of palladium or platinum or selenium and/or tellurium and performing, if desired the dehalogenation and hydrogenation in one step.

As a carrier e.g. active charcoal, silica or aluminum oxide can be used.

In order to prepare the noble metal-containing catalyst one may proceed by treating the aqueous suspension of palladium or platinum on a carrier with a solution or suspension of organic or inorganic selnium or tellurium compounds and optionally by reducing the obtained compound. Such compounds can be selected from salts, oxides and other derivatives, such as selenious acid, diphenyl selenide etc.

Oné may use a different method according to which palladium or platinum salts and selenium or tellurium compounds may be dissolved in acidic water and a carrier, preferably active charcoal can be added to the carrier, followed by reduction.

The noble metal content of the catalyst may vary between 1 to 30% by weight, preferably 5 to 10% by weight, the used noble metal can be selected from palladium and platinum and the amount of the alloying components may vary between 1 to 70% by weight related to the amount of the noble metal content.

As a solvent preferably lower alcohols, ketones, N,N-dialkyl amides, water and mixtures thereof may be used. It is not necessary to dissolve the starting material completely.

According to a preferred method methacycline may be prepared by saturating chloromethacycline with equimolar hydrogen gas at a pressure of 0.1–0.3 MPa in the presence of an alloy catalyst selected from palladium-selenium, palladium-tellurium, platinum-selenium and platinum-tellurium by using the catalyst in an amount of 1:0.01–0.2 related to the weight of chloromethacycline, wherein the amount of the alloying components amounts to 20–70% by weight related to the noble metal content.

Methacycline may be recovered from the reaction mixture by any known method in the form of a base, acid addition salt or complex.

The main advantages of the dehalogenation according to the present invention are: dehalogenation can be performed without side reactions, the conversion of methacyclines to 5-12a lactones can be suppressed, the reaction takes place at atmospheric pressure and room temperature within a short time, the catalyst can be prepared simply and it is not pyrophoric or its activity does not weaken under storing or in the course of the reaction, thus it can be used several times without regeneration, thus the catalyst costs of the process are minimal, and almost negligible.

In order to obtain doxycycline, methacycline or chloromethacycline or a salt thereof can be treated with hydrogen gas in the presence of an alloy catalyst consisting of palladium-selenium, palladium-tellurium, platinum-selenium or platinum-tellurium at a pressure of 0.1–1.0 MPa with an amount of catalyst of 1:0.05–0.5, preferably 0.15–0.25 related to the weight of methacycline, the amount of the alloying components is 1 to 40% by weight.

If chloromethacycline or salts thereof are used as starting material then dehalogenation and the selective saturation of the double bond can be performed in one single step. As a solvent lower alcohol, ketones, dimethylformamide, water and mixtures thereof are used.

When the reaction is terminated the catalyst is filtered and may be used for further reactions. The product may be isolated from the filtrate by any known method, such as in the form of a salt of hydrogen halogenic acid, 5-sulfo salicylic acid or in the form of hyclates.

The main advantages of the process for the preparation of doxycycline are as follows:
the saturation of the exocyclic methylene bond in methacycline takes place substantially stereoselectively, i.e. the β-isomer content is reduced in doxycycline below 1% by weight (according to HPLC),
in the reactions starting with chloromethacycline dehalogenation and hydrogenation can be carried out in one single technological step, the reaction can be performed at atmospheric pressure and room temperature within a short time, the catalyst can be rapidly prepared simply, it is not pyrophoric, and its activity does not decrease under storing or in the course of the hydrogenation reaction and thus the catalyst costs of the process are minimal, almost negligible, the process may be continuous, the isomerization side reactions occurring in heterogeneous catalytical reactions, causing intensive decomposition are suppressed and therefore doxycycline can be obtained with good yield. This experience is highly surprising as the selenium is known to act as a catalyst in oxidation and isomerization reactions.

Further details of the invention can be found in the following Examples:

EXAMPLE 1

10 g of 10% by weight palladium/charcoal catalyst are suspended in 100 ml of water and 0.1 to 0.7 g of selenious acid are added as desired and the mixture is subjected to hydrogenation at room temperature under stirring. The mixture is then filtered, washed with water and acetone and dried. The activity of the catalyst is measured.

EXAMPLE 2

1.33 g of palladium(II)chloride and 0.2–0.7 g of tellurium(IV)oxide are dissolved in 100 ml of 6N hydrochloric acid, whereafter 10 g of charcoal are added and the mixture is stirred for 3 hours and hydrogenated with hydrogen gas. The catalyst is filtered, washed to neutral and dried. Its activity is measured.

EXAMPLE 3

5 g of 10% by weight palladium/charcoal catalyst are suspended in 50 ml of ethanol, and as desired 0.15–1 g of diphenyl selenide are added, the suspension is boiled for 30 minutes, the catalyst is filtered and dried. Its activity is measured.

EXAMPLE 4

10 g of 5% by weight palladium/silica catalyst are suspended in 100 ml of water and as desired 0.1–0.4 g of selenious acid are added and we further proceed as given in Example 1. The activity is measured.

EXAMPLE 5

10 g of 5% by weight platinum/active charcoal catalyst are suspended in 100 ml of water and as desired 0.05 g to 0.4 g of selenious acid are added and we further proceed as disclosed in Example 1.

EXAMPLE 6

1.77 g of palladium(II)chloride and as desired 0.1–0.75 g of selenium dioxide are dissolved in 80 ml of 12N hydrochloric acid and 5 g of silicagel are added, the mixture is hydrogenated, filtered and dried. Its activity is measured.

The activity of the catalysts prepared according to the above Examples are qualified by a method known per se, by hydrogenating a cyclohexene model compound.

PREPARATION OF METHACYCLINE

EXAMPLES 7 TO 12

20 g of 11a-chloro-methacycline-p-toluene-sulfonate are reacted with hydrogen gas in 200 ml of solvent by using 1–3 g alloy on a catalyst carrier at room temperature at a pressure of 0.1–0.3 MPa. When the equimolar amount of hydrogen is taken up, the catalyst is filtered off, and working up may be performed as desired as follows:

(a) 20 g of 5-sulfosalicylic acid are added, it is crystallized and methacycline sulfosalicylate is isolated, or (b) the filtrate is evaporated in vacuo, and 75 ml of methanol and 7.5 g of p-toluene sulfonic acid are added to the residue. The mixture is crystallized and methacycline tosylate is isolated, or (c) the filtrate is evaporated in vacuo and 50 ml concentrated hydrochloric acid are added and methacycline hydrochloride is isolated. Yield: 85–95%.

The quality of the products is thin layer chromatographically homogeneous (developing agent: a 95:5 mixture of tetrahydrofuran and water) on a silicagel carrier plate impregnated with a buffer of pH=6. Active ingredient content by biological value testing: 100%.

The details are shown in Table I.

TABLE I

| Example No. | Catalyst+ pressure | Solvent++ | Working up method | Product | Yield |
|---|---|---|---|---|---|
| 7 | 1 g 5% Pd/charcoal Se 20%, 0.1 MPa | methanol-water 3:1 | (a) | 20 g methacycline-sulfosalicylate | 95.6% |
| 8 | 1 g 5% Pt/charcoal Se 25%, 0.2 MPa | acetone-water 4:1 | (a) | 18.8 g methacycline-sulfosalicylate | 90.0% |
| 9 | 2 g 10% Pd/charcoal Se 40%, 0.3 MPa | methyl-ethyl-ketone/water 4:1 | (b) | 17.9 g methacycline-tosylate | 95.6% |
| 10 | 2 g 3.5% Pd/charcoal Te 50%, 0.3 MPa | methyl-ethyl-ketone/water 4:1 | (b) | 16.4 g methacycline tosylate | 88.0% |
| 11 | 2 g 5% Pd/silicagel Se 30%, 0.3 MPa | acetone-water 4:1 | (c) | 12.45 g methacycline hydrochloride | 87.0% |
| 12 | 1.5 g 10% Pd/charcoal Se 30%, 0.2 MPa | acetone-water 4:1 | (c) | 12.2 g methacycline hydrochloride | 85.0% |

+The noble metal content of the catalyst related to the weight of catalyst is given in % by weight and the amount of the alloying metal is determined in % by weight related to the noble metal content.
++The composition of the solvent is given in % by volume.

PREPARATION OF DOXYCYCLINE

EXAMPLES 13 TO 20

47.3 g of methacycline hydrochloride or 63.6 g of methacycline p-toluene sulfonate are hydrogenated in 500–580 ml of solvent by using 3.5 to 10 g of an alloy catalyst on carrier at room temperature and a pressure of 0.1 to 1.0 MPa until the hydrogen uptake is completed. After filtering off the catalyst the filtrate can be worked up as follows:

(a) 50 g of 5-sulfosalicylic acid are added to the filtrate and the product is crystallized and filtered, dried.

Doxycycline sulfosalicylate is obtained as a product, or
(b) the filtrate is evaporated in vacuo, 250 ml methanol and 25 g of p-toluene sulfonic acid are added to the residue, the mixture is crystallized and doxycycline tosylate is isolated, or
(c) the filtrate is evaporated in vacuo, 180 ml of ethanol and 30 ml of hydrochloric acid are added to the residue and after dissolving and clarification 50 ml of hydrochloric acid and ethanol in hydrochloric acid are added to the filtrate. The mixture is crystallized and doxycycline hyclate is isolated, or
(d) the filtrate is evaporated to dryness in vacuo, 250 ml of acetone are added to the residue and by introducing hydrochloric acid gas the doxycycline hydrochloride is recovered.

Yield: 80–90%. Quality of the product is homogeneous according to thin layer chromatography.

Active ingredient content by biological value testing: 100%.

Ratio of α-isomer: 99%, ratio of β-isomer: 0–0.6%.
The details are shown in Table II.

MPa until the hydrogen uptake is completed. After filtering off the catalyst the filtrate can be worked up as follows:
(a) 50 g of 5-sulfosalicylic acid are added to the filtrate and the product is crystallized and filtered, dried. Doxycycline sulfosalicylate is obtained as a product, or
(b) the filtrate is evaporated in vacuo, 250 ml methanol and 25 g of p-toluene sulfonic acid are added to the residue, the mixture is crystallized and doxycycline tosylate is isolated, or
(c) the filtrate is evaporated in vacuo, 180 ml of ethanol and 30 ml of hydrochloric acid are added to the residue and after dissolving and clarification 50 ml of hydrochloric acid and ethanol in hydrochloric acid are added to the filtrate. The mixture is crystallized and doxycycline hyclate is isolated, or
(d) the filtrate is evaporated to dryness in vacuo, 250 ml of acetone are added to the residue and by introducing hydrochloric acid gas the doxycycline hydrochloride is recovered.

Yield: 80–90%. Quality of the product is homogene-

TABLE II

| Example No. | Catalyst+ pressure | Solvent++ | Working up method | Product | Yield |
|---|---|---|---|---|---|
| 13 | 10 g 5% Pd/charcoal Se 5%, 0.3 MPa | acetone water 4:1 | (a) | 62 g doxycycline-sulfosalicylate | 89% |
| 14 | 5 g 5% Pt/charcoal Se 8%, 0.3 MPa | methyl-ethyl-ketone/water 4:1 | (a) | 61.5 g doxycycline-sulfosalicylate | 88% |
| 15 | 8 g 10% Pd/charcoal Se 20%, 0.4 MPa | acetone-water 4:1 | (b) | 54.1 g doxycycline-tosylate | 88% |
| 16 | 5 g 3.5% Pd/charcoal Te 15%, 0.5 MPa | methyl-ethyl-ketone/water 4:1 | (b) | 50.5 g doxycycline-tosylate | 82% |
| 17 | 10 g 5% Pd/silicagel Se 10%, 0.3 MPa | methyl-ethyl-ketone/water 4:1 | (c) | 43.1 g doxycycline-hyclate | 85% |
| 18 | 4 g 10% Pd/charcoal Se 15%, 0.3 MPa | acetone-water 4:1 | (c) | 42.6 g doxycycline-hyclate | 83% |
| 19 | 6 g 10% Pd/charcoal Se 12%, 0.2 MPa | acetone-water 4:1 | (d) | 40.6 g doxycycline-hydrochloride | 88% |
| 20 | 10 g 5% Pd/silicagel Se 7%, 0.3 MPa | methyl-ethyl-ketone/water 4:1 | (d) | 39.2 g doxycycline-hydrochloride | 85% |

+The nobel metal content of the catalyst related to the weight of catalyst is given in % by weight and the amount of the alloying metal is determined in % by weight related to the noble metal content.
++The composition of the solvent is given in % by volume.

EXAMPLES 21–28

66.7 g of 11a-chloro-methacycline-p-toluene-sulfonate are subjected to hydrogenation in 500–580 ml of solvent by using 3.5 to 10 g of an alloy catalyst on carrier at room temperature and a pressure of 0.1 to 1.0 ous according to thin layer chromatography.
Active ingredient content by biological value testing: 100%.

Ratio of α-isomer: 99%, ratio of β-isomer: 0–0.6%.
The details are shown in Table III.

TABLE III

| Example No. | Catalyst+ | Solvent++ | Pressure MPa | Working up method | Product | Yield |
|---|---|---|---|---|---|---|
| 21 | 10 g 5% Pd/charcoal Se 5% | acetone-water 4:1 | 0.2–0.4 | a/ | 61.5 g doxycycline sulfosalicylate | 88% 88% |
| 22 | 5 g 5% Pd/charcoal Se 8% | methyl-ethyl-ketone/water 4:1 | 0.2–0.4 | a/ | 59.2 g doxycycline sulfosalicylate | 85% |
| 23 | 8 g 10% Pd/charcoal Se 20% | acetone-water 4:1 | 0.3–0.5 | b/ | 53.6 g doxycycline-tosylate | 87% |
| 24 | 5 g 3.5% Pd/charcoal Te 15% | methyl-ethyl-ketone/water 4:1 | 0.4–0.5 | b/ | 50.5 g doxycycline-tosylate | 82% |
| 25 | 10 g 5% Pd/silicagel Se 10% | methyl-ethyl-ketone/water 4:1 | 0.2–0.4 | c/ | 42.1 g doxycycline-hyclate | 82% |
| 26 | 4 g 10% Pd/charcoal Se 15% | acetone-water 4:1 | 0.4–0.5 | c/ | 42.1 g doxycycline-hyclate | 82% |
| 27 | 6 g 10% Pd/charcoal Se 12% | acetone-water 4:1 | 0.2–0.3 | d/ | 39.2 g doxycycline-hydrochloride | 85% |
| 28 | 10 g 5% Pd/silicagel Se 7% | methyl-ethyl-ketone/water 4:1 | 0.2–0.3 | d/ | 38.3 g doxycycline-hydrochloride | 83% |

+The nobel metal content of the catalyst related to the weight of catalyst is given in % by weight and the amount of the alloying metal is determined in % by weight related to the nobel metal content.
++The composition of the solvent is given in % by volume.

We claim:
1. Process for the preparation of tetracycline derivatives of the formula

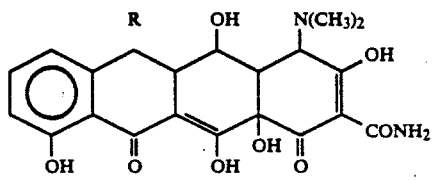

and acid addition salts thereof wherein R stands for —CH₃ by dehalogenating and hydrogenating chloromethacycline or acid addition salts thereof of the formula

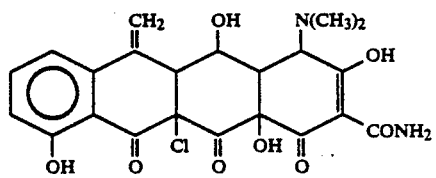

or by hydrogenating methacycline or acid addition salts thereof of the formula

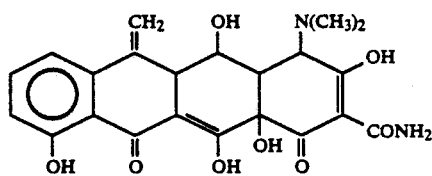

by a treatment with hydrogen gas in the presence of a noble metal alloy catalyst on a carrier and an organic solvent which comprises performing hydrogenating under pressure of 0.1–1.0 MPa with an alloy catalyst consisting of either palladium or platinum and selenium, tellurium or a mixture thereof used at a ratio of 1:0.01–0.5 related to the amount of the starting tetracycline and carrying out, if desired dehalogenation and hydrogenation in one step.

2. Process as claimed in claim 1 which comprises preparing methacycline by saturating chloromethacycline with equimolar hydrogen gas in the presence of an alloy catalyst of palladium-selenium, palladium-tellurium or platinum-selenium or platinum-tellurium on a carrier under a pressure of 0.1–0.3 MPa at a ratio of 1:0.01–0.2 catalyst related to the amount of chloromethacycline, wherein the amount of selenium, tellurium or a mixture thereof amounts to 20–70% by weight related to the amount of palladium or platinum.

3. Process as claimed in claim 1 which comprises preparing doxycycline by treating methacycline or salts thereof with hydrogen gas in the presence of an alloy catalyst consisting of palladium-selenium, palladium-tellurium, platinum-selenium or platinum-tellurium on a carrier at a pressure of 0.1–1 MPa at a ratio of 1:0.05–5 catalyst related to the weight of methacycline, wherein the amount of the alloying components amounts to 1–40% by weight.

4. Process as claimed in claim 1 which comprises preparing doxycycline by treating chloromethacycline or salts thereof with hydrogen gas in the presence of an alloy catalyst consisting of palladium-selenium, palladium-tellurium, platinum-selenium or platinum-tellurium on a carrier at a pressure of 0.1–1 MPa at a ratio of 1:0.05–5 catalyst related to the weight of methacycline, wherein the amount of the alloying components amounts to 1–40% by weight.

5. Process as claimed in claim 2 which comprises using water, alcohols, ketones or mixtures thereof as a solvent.

6. Process as claimed in claim 1 which comprises using as alloys for hydrogenation alloys which contain 1–70% by weight of selenium or tellurium and 99–30% by weight of palladium or platinum.

* * * * *